United States Patent
Yamamoto et al.

[11] Patent Number: 5,856,622
[45] Date of Patent: Jan. 5, 1999

[54] CLAMP-ON TYPE ULTRASONIC FLOW METER AND A TEMPERATURE AND PRESSURE COMPENSATION METHOD THEREIN

[75] Inventors: Toshihiro Yamamoto; Satoru Nakamura; Akio Miyamoto, all of Kawasaki, Japan

[73] Assignee: Fuji Electric Co., Ltd., Kawasaki, Japan

[21] Appl. No.: 616,907

[22] Filed: Mar. 19, 1996

[30] Foreign Application Priority Data

Mar. 20, 1995 [JP] Japan ................................. 7-060237

[51] Int. Cl.⁶ ............................................. G01F 1/00
[52] U.S. Cl. .................................. 73/861.28; 364/510
[58] Field of Search ...................... 73/861.27, 861.28, 73/861.29, 861.31; 364/510; 367/902

[56] References Cited

U.S. PATENT DOCUMENTS

| | | | |
|---|---|---|---|
| 5,152,174 | 10/1992 | LaBuddle . | |
| 5,280,728 | 1/1994 | Sato et al. | 73/861.28 |
| 5,442,592 | 8/1995 | Toda et al. | 73/861.27 |
| 5,546,813 | 8/1996 | Hastings et al. | 73/861.29 |

FOREIGN PATENT DOCUMENTS

| | | |
|---|---|---|
| 0 012 160 A1 | 6/1980 | European Pat. Off. . |
| 0 200 896 A2 | 12/1986 | European Pat. Off. . |
| 0 605 944 A2 | 7/1994 | European Pat. Off. . |
| PTC/GB88/ 00328 | 11/1988 | WIPO . |
| WO 88/08516 | 11/1988 | WIPO ............................. 73/861.28 |
| PCT/US92/ 06180 | 2/1993 | WIPO . |

*Primary Examiner*—Ronald L. Biegel
*Attorney, Agent, or Firm*—Finnegan, Henderson, Farabow, Garrett & Dunner, L.L.P.

[57] ABSTRACT

A ratio C of sonic speed in a fluid to a sinusoidal value at an incident angle of sonic waves from the pipe to the fluid is designated as a basic unknown quantity. A distance D between the opposite inner wall surfaces of the pipe, a thickness $t_p$ of the pipe wall, a projection length $t_w$ of sound rays in the oblique wedge projected onto a plane orthogonal to the center axis of the pipe, and sonic speed $C_w$, $C_p$ in the oblique wedge and the pipe wall are used as given values. A propagation time τ of ultrasonic waves through the oblique wedge and the pipe wall is treated as a variable. The value C is determined in course of calculating a projection length L of sound rays between the ultrasonic transducers projected onto the center axis of the pipe by a gradual approximation, which is determined as a given value. Then, a refraction angle $θ_f$ of sonic waves from the pipe wall to the fluid and a propagation time τ of ultrasonic waves through the oblique wedge of the ultrasonic transducer are determined based on the value C. These values and a propagation time of ultrasonic waves between the ultrasonic transducers obtained by a measurement are applied to a basic equation to derive a flow velocity of the fluid in the pipe at temperature and pressure under a service condition.

14 Claims, 7 Drawing Sheets

CORRECTED DATA

CALCULATED VALUE OF
SONIC SPEED IN WATER

CORRECTED DATA

CALCULATED VALUE OF
SONIC SPEED IN WATER

○ : SONIC SPEED CALCULATED FROM T0
■ : SONIC SPEED CALCULATED WITH
    REFERENCE TO STEAM TABLES

CLAMP-ON TYPE ULTRASONIC FLOW METER AND A TEMPERATURE AND PRESSURE COMPENSATION METHOD THEREIN

BACKGROUND OF THE INVENTION

The present invention relates to a clamp-on type ultrasonic flow meter and a method of compensating for influences exerted by temperature and pressure of a fluid and by temperature of a detector in an ultrasonic flow meter for measuring a flow velocity or a flow amount of a fluid based on a difference in propagation time of ultrasonic waves through the fluid caused by a flow of the fluid, and more particularly, to such a compensation method for use in a clamp-on type ultrasonic flow meter having ultrasonic transducers closely attached on an outer wall surface of an existing pipe for measuring a flow velocity of a fluid flowing through the pipe.

When ultrasonic waves propagate through a flowing fluid, the ultrasonic waves are affected by the fluid flow so that a propagation time measured when the ultrasonic waves are directed from the upstream side to the downstream side of the fluid flow is different from that measured when directed from the downstream side to the upstream side of the fluid flow. Since the difference in the propagation time is in a proportional relationship with the flow velocity of the fluid, an ultrasonic flow meter utilizes this relationship for measuring the flow velocity of the fluid.

In plant facilities for water treatment, iron manufacturing, chemical processing, district air conditioning, and the like, liquids such as water, corrosive fluids and the like are supplied through pipes. If a flow amount of a fluid flowing through an existing pipe needs to be measured, a clamp-on type ultrasonic flow meter may be employed, wherein a pair or more of ultrasonic transducers are mounted closely on the outer wall surface of the existing pipe such that ultrasonic waves are transmitted and received through the pipe wall to measure the flow amount of the fluid flowing through the pipe.

FIGS. 6A and 6B illustrate a basic configuration of a detector unit of a clamp-on type ultrasonic flow meter. First, the principle of the ultrasonic flow meter for measuring a flow velocity of a fluid will be explained with reference to FIGS. 6A, 6B. FIG. 6A illustrates the whole configuration of the detector unit, and FIG. 6B illustrates in greater detail an ultrasonic transducer mounting member.

A detector unit 100 of the clamp-on type ultrasonic flow meter illustrated in FIG. 6A includes ultrasonic oscillators 1a, 1b, and oblique wedges 2a, 2b for acoustically coupling a fluid 4 flowing in a pipe 3 to the ultrasonic oscillators 1a, 1b. The ultrasonic oscillators and the oblique wedges are acoustically coupled to constitute ultrasonic transducers 10a, 10b.

When a driving pulse is applied to the ultrasonic oscillator 1a of the upstream ultrasonic transducer 10a in the detector unit 100 of the ultrasonic flow meter for causing the ultrasonic oscillator 1a to oscillate, ultrasonic waves are emitted therefrom and propagate through the oblique wedge 2a and the pipe 3 to the fluid 4 flowing in the pipe 3. Then, the ultrasonic waves propagating through the fluid 4 in the pipe reach the opposite wall of the pipe 3, and then are guided by the oblique wedge 2b, lead by the ultrasonic transducer 10b, now set in a receiver mode, and received by the ultrasonic oscillator 1b.

The ultrasonic waves emitted from the ultrasonic oscillator 1a are elastic waves having a certain spreading and directivity. However, it is a general tendency that an ultrasonic wave source and a receiver unit are regarded as points at the center of the elastic waves and a propagation path of the wave front is treated as an acoustic line passing through these two points. In this event, at a location in a propagation medium where sonic speed changes discontinuously, a law of reflection and refraction is satisfied with respect to the propagation of wave motion. Such a model is generally referred to as a point sound source model.

In the following, an analysis will be made on a process of the propagation of ultrasonic waves in the detector unit 100 of the clamp-on type ultrasonic flow meter configured as illustrated in FIG. 6, on the basis of the point sound source model, in order to explain the relationship between a propagation time of ultrasonic waves propagating from one ultrasonic transducer to the other and a flow velocity of a fluid flowing through the pipe on which the detector unit is installed.

Assuming that $T_1$ represents a forward direction propagation time of ultrasonic waves emitted from the upstream ultrasonic transducer 10a and reaching the downstream ultrasonic transducer 10b, and $T_2$ represents a backward direction propagation time of the ultrasonic waves emitted from the downstream ultrasonic transducer 10b and received by the upstream ultrasonic transducer 10a, the propagation times $T_1$, $T_2$ are given by the following Equations (1) and (2), respectively, which express that a propagation distance of the ultrasonic waves is divided by effective sonic speed, i.e., the sum of sonic speed and a component of a flow velocity of the fluid in the ultrasonic wave propagating direction:

[Equation (1)]

$$T_1 = (D/\cos\theta_f)/(C_f + V\sin\theta_f) + \tau \tag{1}$$

[Equation (2)]

$$T_2 = (D/\cos\theta_f)/(C_f - V\sin\theta_f) + \tau \tag{2}$$

where

D: a distance between opposite inner wall surfaces of the pipe through which the ultrasonic waves pass (inner diameter if the pipe has a circular shape in cross-section);

$\tau$: a propagation time of the ultrasonic waves passing through the pipe and the oblique wedges;

$C_f$: sonic speed in the fluid;

V: an average flow velocity of the fluid on sound rays; and $\theta f$: a refraction angle of the ultrasonic waves from the pipe to the fluid.

Thus, a difference $\Delta T$ between the forward and backward propagation times $T_1$ and $T_2$ is first given by the following Equation (3a). However, when a fluid under measurement is water, sonic speed $C_f$ is approximately 1,500 m/s whereas the flow velocity V of the fluid in the pipe rarely exceeds 30 m/s at the highest, so that $C_f^2 \gg V^2$ stands, and therefore an approximation expressed by Equation (3b) is satisfied at very high accuracy:

[Equation (3)]

$$\Delta T = T_2 - T_1 = (2DV\tan\theta_f)/(C_f^2 - V^2\sin^2\theta_f) \tag{3a}$$

$$\approx (2DV\tan\theta_f)/C_f^2 \quad (\because C_f^2 \gg V^2) \tag{3b}$$

By substituting zero for the flow velocity V of a fluid in Equation (1) or Equation (2), a propagation time $T_0$ of the fluid in a stationary state is given by Equation (4). On the other hand, by adding Equation (1) to Equation (2) and applying the approximation of the relationship between sonic speed $C_f$ in the fluid and the fluid flow velocity V to the addition result, Equation (5) is derived in the same form as Equation (4). As a result, the propagation time $T_0$ of the fluid at a stationary state may be approximated by an average value of measured propagation times of ultrasonic waves in the forward and backward directions, detected between the ultrasonic transducers $1a$, $1b$ of the detector unit $100$ of the ultrasonic flow meter when the fluid is flowing.
[Equation (4)]

$$T_0 = (D/\cos\theta_f)/C_f + \tau \qquad (4)$$

[Equation (5)]

$$(T_1 + T_2)/2 = (DC_f/\cos\theta_f)/(C_f^2 - V^2\sin^2\theta_f) + \tau \qquad (5)$$
$$\approx (D/\cos\theta_f)/C_f + \tau = T_0$$

By substituting $C_f$ from Equation (3b) and Equation (4), Equation (6) expressing an average flow velocity on sound rays of the fluid in the pipe is derived:
[Equation (6)]

$$V = (D/\sin2\theta_f)\{\Delta T/(T_0-\tau)^2\} \qquad (6)$$

The propagation time difference $\Delta T$ and the propagation time $T_0$ of the fluid in a stationary state may be derived by an approximation based on measured values detected by the detector unit $100$ of the ultrasonic flow meter when the fluid is flowing, as explained above.

On the other hand, between an incident angle $\theta_f$ of sound rays into the fluid and the propagation time $\tau$ of ultrasonic waves through the pipe and the oblique wedges, the relationship explained below is satisfied based on the law of reflection and refraction with respect to the propagation of wave motion.

More specifically, as illustrated in FIG. 6B which is a detailed explanatory diagram of a mounting member for the ultrasonic transducer, assuming:

$t_w$: a length of sound rays in the oblique wedge projected onto a plane perpendicular to the center axis of the pipe;

$t_p$: a thickness of the wall of a pipe;

$C_w$: sonic speed in the material of the oblique wedge;

$C_p$: sonic speed in the material of the pipe;

$\theta_w$: an incident angle of sound rays from the oblique wedge to the pipe;

$\theta_p$: a refraction angle of ultrasonic waves from the oblique wedge to the pipe (i.e., an incident angle of sound rays from the pipe to a fluid);

$\theta_r$: a refraction angle of the ultrasonic waves from the pipe to the fluid, Equation (7) is satisfied based on the law of refraction with respect to the propagation of wave motion at respective interfaces between propagation media of the oblique wedge $2$, the pipe $3$, and the fluid $4$, and a ratio C of sonic speed to the refraction angle ratio (hereinafter, this ratio is called the sonic speed/refraction angle ratio) on the right side is a constant in accordance with the law of refraction.
[Equation (7)]

$$C_w/\sin\theta_w = C_p/\sin\theta_p = C_f/\sin\theta_f = C \text{ (constant)} \qquad (7)$$

The propagation time $\tau$ of ultrasonic waves through the pipe $3$ and the oblique wedges $2$ is expressed by the following Equation (8) which means the sum of the propagation times of the ultrasonic waves on the transmission and reception sides, since the ultrasonic waves pass through these elements on the respective sides.
[Equation (8)]

$$\tau = 2t_w/(C_w\cos\theta_w) + 2t_p/(C_p\cos\theta_p) \qquad (8)$$

In Equation (7), the sonic speed values $C_w$, $C_p$, $C_f$ in the respective media can be previously derived by a search, once service conditions are established for materials used for members such as the oblique wedges $2$ and the pipe $3$, the kind and temperature of a fluid flowing through the pipe $3$, and so on. Also, since the incident angle $\theta_w$ of sound rays from the oblique wedge $2$ to the pipe $3$ has been determined in the design of the oblique wedge $2$, the refraction angle $\theta_p$ of sound rays from the oblique wedge $2$ to the pipe $3$ and the refraction angle $\theta_f$ of sound rays from the pipe $3$ to the fluid can be derived by applying the known values into Equation (7).

Further, the projection length $t_w$ of sound rays in the oblique wedge $2$ projected onto a plane perpendicular to the center axis of the pipe has been determined in the design of the oblique wedge $2$, and the distance D between opposite inner wall surfaces and the thickness $t_p$ of the pipe are also data which is previously obtainable from the standard of pipes or from actual measurements.

The values of the propagation time difference $\Delta T$ and the propagation time $T_0$ of the fluid in a stationary state, derived by an acoustic measurement by the detector unit of the ultrasonic flow meter, associated design values of the detector unit, the incident angle $\theta_f$ of sound rays from the pipe to the fluid, determined by the kind of the fluid flowing through the pipe, and the propagation time $\tau$ of the ultrasonic waves through the pipe and the oblique wedge are substituted into Equation (6) to derive an average flow velocity V on sound rays of the fluid flowing through the pipe on which the detector unit is installed. A flow amount of the fluid in a pipe having a circular shape in cross-section, for example, is calculated by Equation (9):
[Equation (9)]

$$Q = (\pi D^2/4)(1/K)(D/\sin2\theta_f)\{\Delta T/(T_0-\tau)^2\} \qquad (9)$$

K in Equation (9) is a conversion coefficient for the conversion between an average flow velocity on sound rays in the fluid and an average flow velocity on the cross section of the pipe.

The measurement principle of the clamp-on type ultrasonic flow meter has been described hereinabove. For actual installation of the ultrasonic flow meter, the ultrasonic transducers may be mounted on opposite sides of the fluid pipe $3$ such that a propagation path of ultrasonic waves forms a Z-shape, as illustrated in the principle explaining diagram of FIG. 6A, or the ultrasonic transducers may be mounted on the same side on the outer wall surface of the pipe to form a propagation path of ultrasonic waves in a V-shape such that ultrasonic waves emitted from one ultrasonic transducer and reflected by the inner wall surface of the pipe is received by the other ultrasonic transducer mounted on the same side, as illustrated in FIG. 7.

When the ultrasonic transducers are mounted on the same side on the outer wall surface of the fluid pipe, as illustrated in FIG. 7, ultrasonic waves are emitted from one ultrasonic transducer, reciprocate in the diametrical direction of the pipe, and are received by the other ultrasonic transducer. Thus, the relationship between propagation times $T_1$, $T_2$ and the flow velocity V is given by substituting 2D into the distance D between the opposite inner wall surfaces in Equations (1) and (2). It will be understood from this fact that the configuration of the two ultrasonic transducers on the same side is regarded as completely the same as the configuration of those illustrated in FIG. 6 in terms of the principles.

A propagation speed $C_f$ of ultrasonic waves propagating a medium as vertical waves has a relationship with the density ρ and the volumetric elasticity κ of the medium expressed by the following Equation (10).
[Equation (10)]

$$C_f = \sqrt{\kappa/\rho} \qquad (10)$$

Since the density ρ and the volumetric elasticity κ of the medium in Equation (10) vary depending on temperature and pressure of the medium, the propagation speed $C_f$ of ultrasonic waves in the medium also exhibits temperature and pressure dependency. If the medium is gas, its temperature and pressure are in a relationship expressed by the gas state equation.

While the propagation speed $C_f$ of ultrasonic waves in a liquid also exhibits dependency for temperature and pressure, there is no simple equation expressing a relationship which is commonly satisfied irrespective of the kind of liquids, as the gas state equation. Thus, actual measurements have been made for representative particular liquid materials to obtain data associated with the relationship.

A simplified state diagram for water, which has been most frequently applied to obtain the above relationship of liquid, is shown in FIG. 8. It should be noted that this diagram is quoted from the steam tables published by Japan Society of Mechanical Engineers (1980).

As can be seen from FIG. 8, when water temperature is gradually raised from the vicinity of 0° C., sonic speed in water also rises to approximately 70° C., exhibits a maximum value in the vicinity of 75° C., and then begins to decrease. Stated another way, water temperature is a two-valued function of sonic speed in water, so that sonic speed in water exhibits the same value at different two temperature levels. Also, as the pressure is increased, sonic speed in water also increases, so that sonic speed in water has larger dependency for pressure in a higher temperature range.

Although not so remarkable as sonic speed in liquid, sonic speed in solid materials, respectively constituting the oblique wedges and the pipe wall, also exhibits temperature dependency. Generally, as the temperature is raised, sonic speed in these materials decreases, as shown in FIG. 9.

As explained above, since sonic speed of ultrasonic waves propagating not only a liquid flowing through a pipe of a clamp-on type ultrasonic flow meter but also the oblique wedges and the pipe wall constituting the detector unit of the flow meter exhibits the temperature dependency, measurement errors and variations in output will be remarkable unless measured values of sonic speed are subjected to compensation for temperature and/or pressure, if temperature and/or pressure of the liquid vary or temperature of the oblique wedges and the pipe varies due to the action of liquid temperature and environmental temperature.

Since an average value $T_0$ of the propagation times in the forward and backward directions and sonic speed in liquid is in the relationship expressed by Equation (5) when the liquid pressure is held constant. Thus, for a liquid with a known relationship between sonic speed and temperature, if an average value $T_0$ of the propagation times of ultrasonic waves through the liquid in the forward and backward directions is measured, the temperature of the liquid can be derived from the measured value through the sonic speed, thus providing additionally the value of a temperature change ratio of sonic speed under the measuring conditions. Using a function expressing this relationship, when an average value $T_{0S}$ of propagation times measured at reference pressure and temperature levels is designated a reference for the propagation time, the relationship between a difference of an average value $T_0$ of the propagation times from the reference value $T_{0S}$ and sonic speed in a liquid, i.e., the relationship between the difference $(T_0-T_{0S})$ and a refraction angle $\theta_f$ can be previously derived from Equation (7). Thus, in a conventional clamp-on type ultrasonic flow meter, the relationship between a difference portion of a propagation time average value $T_0$ from the reference value $T_{0S}$ and a refraction angle $\theta_f$ or a change amount of its trigonometric function are stored in a flow velocity calculation unit, such that upon detecting a change in the propagation time average value $T_0$, sonic speed in a fluid under measuring conditions can be calculated based on the stored data in the flow velocity calculation unit to derive a temperature compensated flow velocity value.

For pressure compensation, on the other hand, a pressure sensor is separately provided for measuring fluid pressure of a liquid having a known relationship between sonic speed and pressure, such that sonic speed is corrected based on a detected pressure value of the pressure sensor.

In the conventional clamp-on type ultrasonic flow meter as described in the previous paragraph, if the relationship between sonic speed and pressure is not known for a fluid under measurement, it is impossible to correct measurement errors due to changes in pressure and variations in output caused by fluctuations in pressure. In addition, even if the relationship between sonic speed and pressure is known, a pressure sensor must be provided for measuring a fluid pressure to correct the sonic speed in terms of pressure based on the measured value.

Also, for a fluid under measurement exhibiting a large temperature change, a temperature correction may be carried out to provide more accurate measured values, only when the relationship between sonic speed in the fluid under measurement and temperature is previously known. However, if the relationship between sonic speed and temperature is unknown, an appropriate temperature correction cannot be made for providing highly accurate measured values.

Moreover, even if the relationship between sonic speed in the fluid and the temperature is known, means for measuring fluid temperature or a physical amount equivalent to the fluid temperature is required to correct sonic speed in terms of temperature based on a measured value from the measuring means. Particularly, when measuring a fluid such as water in which sonic speed exhibits a maximum value and has temperature dependency largely differing on one and the other sides of the maximum value, a correction region must be determined based on a detected temperature value of the fluid under measurement to modify compensation coefficients.

Further, in the prior art, propagation paths of ultrasonic waves through oblique wedges in the ultrasonic transducers and through a pipe material are fixed for convenience, such that a constant value derived from sonic speed over the respective path length in the respective materials at a given temperature is designated a propagation time τ of ultrasonic waves through the oblique wedges and the pipe. However, even if sonic speed of ultrasonic waves through the materials of the oblique wedges and the pipe is identical, changes in temperature and/or pressure of the fluid under measurement causes the propagation paths of ultrasonic waves through the oblique wedges and the pipe to change. Also, although not so remarkable as in the case of liquid, sonic speed of ultrasonic waves through the respective solid materials of the oblique wedges and the pipe varies depending on temperature. Generally, as the temperature rises, sonic speed in the respective materials decreases. Thus, variations in temperature and pressure of the fluid, or variations in temperature of the oblique wedges and the pipe due to the action of fluid temperature and environmental temperature will result in measurement errors and variations in output.

SUMMARY OF THE INVENTION

It is an object of the present invention to provide a temperature and pressure compensation method for clamp-on type ultrasonic flow meters which is capable of solving the problems inherent to a temperature and pressure compensation method in conventional clamp-on type ultrasonic flow meters as described above. Specifically, the temperature and pressure compensation method of the present invention calculates the values of various parameters required for correction, by the use of the value of a propagation time measured by an acoustic measurement which does not require previously calculation of data indicative of the influence of temperature and pressure on sonic speed or measurement of the temperature and pressure of a fluid under measurement, and respective values determined by the design of the ultrasonic transducers and a pipe on which the flow meter is to be installed. The present invention corrects the influence of temperature and pressure on sonic speed in a medium, through which ultrasonic waves propagate, to provide a corrected value as close as possible to a true value of a flow velocity of the fluid, thus improving the accuracy of the clamp-on type ultrasonic flow meter.

In the temperature and pressure compensation method of the present invention, it is assumed that a detector unit of a clamp-on type ultrasonic flow meter is configured as illustrated in FIG. 6, and sonic speed in a fluid under measurement exhibiting large temperature dependency and an incident angle of ultrasonic waves from a pipe into the fluid, depending on the sonic speed, are basic unknown parameters, at temperature and pressure under service conditions of the clamp-on type ultrasonic flow meter. A value C of a ratio of sonic speed in the fluid to a sinusoidal value at an incident angle of ultrasonic waves propagating from a pipe to the fluid is determined, by the use of given values of a distance D between opposite inner wall surfaces of the pipe, a thickness of the pipe $t_p$, a projection length $t_w$ of sound rays in the oblique wedges projected onto a plane perpendicular to the axis of the pipe, and sonic speed $C_w$, $C_p$ in the oblique wedges and in the wall of the pipe, in course of calculating, in gradual approximation, a projection length L of sound rays between the ultrasonic transducers projected onto the axis of the pipe, determined as a given value depending on the arrangement of the ultrasonic transducers on the outer wall surface of the pipe, with a propagation time τ of ultrasonic waves through the oblique wedges and the wall of the pipe used as a variable. Then, based on this value C calculated in the gradual approximation, a refraction angle $\theta_f$ of ultrasonic waves from the pipe wall to the fluid and a propagation time τ of ultrasonic waves through the pipe wall and the oblique wedges in the ultrasonic transducers are determined in the basic Equation (6) for calculating the flow velocity. With these values and the value of the propagation time of sonic waves between the ultrasonic transducers derived by a measurement are applied to the basic Equation (6) to derive the flow velocity of the fluid in the pipe at temperature and pressure under a service condition.

The principle of the temperature and pressure compensation method implemented by the means described in the previous paragraph will be next explained.

Assuming that a length of sound rays between the ultrasonic transducers 10a, 10b in the detector unit of the clamp-on type ultrasonic flow meter having the configuration illustrated in FIG. 6 projected in the direction of the center axis of the pipe is represented by L, the value of L is given by Equation (11) based on geometric conditions. In Equation (11), reference numerals explained in connection with FIG. 6 are commonly used.

[Equation (11)]

$$L = 2t_w \tan\theta_w + 2t_p \tan\theta_p + D\tan\theta_f \qquad (11)$$

Since $0 < \theta_w, \theta_p, \theta_f < 90°$, Equation (7) is used to substitute $\theta_w, \theta_p, \theta_f$ from Equation (11), the following Equation (12) is derived:

[Equation (12)]

$$L = 2t_w(C_w/\sqrt{C^2 - C_w^2}) + 2t_p(C_p/\sqrt{C^2 - C_p^2}) + D(C_f/\sqrt{C^2 - C_f^2}) \qquad (12)$$

Also, by substituting $\theta_f$ from Equation (7) and Equation (4) to derive $C_f$, Equation (13) is given.

[Equation (13*)]

$$C_f = \sqrt{(C^2/2) \pm \sqrt{(C^2/2)^2 - C^2 D^2/(T_0 - \tau)^2}} \qquad (13^*)$$

In general, the relation $0 < \theta < 45°$ is satisfied in order to increase the effect of injection of the ultrasonic waves. Since $\theta_f$ is preferably about 23°, the minus (−) sign is selected in the sign (±) of [Equation (13*)].

[Equation (13)]

$$C_f = \sqrt{(C^2/2) - \sqrt{(C^2/2)^2 - C^2 D^2/(T_0 - \tau)^2}} \qquad (13)$$

On the other hand, by substituting $\theta_w, \theta_p$ from Equation (7) and Equation (8), the following Equation (14) is given.

[Equation (14)]

$$\tau = 2t_w\{C/(C_w\sqrt{C^2 - C_w^2})\} + 2t_p\{C/(C_p\sqrt{C^2 - C_p^2})\} \qquad (14)$$

In each of Equations (12), (13), (14), a propagation time $T_0$ of ultrasonic waves between the ultrasonic transducers through a fluid in a stationary state is derived as an average of measured values of propagation times of ultrasonic waves between the ultrasonic transducers in both directions when the fluid is flowing in the pipe, as explained above in connection with Equation (5). The distance D between the opposite inner wall surfaces of the pipe and the thickness of the pipe $t_p$ are known from the standard or actual measurement of the pipe on which the ultrasonic transducers are mounted. The projection length L of sound rays between the ultrasonic transducers projected onto the axis of the pipe is calculated using associated values determined by the design of the ultrasonic transducers, based on a measured value of the spacing between the mounted positions of the ultrasonic transducers 10a, 10b. The projection length $t_w$ of sound rays in the oblique wedge 2 projected onto a plane perpendicular to the axis of the pipe is also a value determined by the design of the oblique wedges 2.

On the other hand, for the propagation speeds $C_w$, $C_p$ of ultrasonic waves through the oblique wedge and the pipe wall respectively made of known materials, data can be obtained including temperature dependency for a temperature range practically used corresponding to these materials. However, for fluids, particularly for liquid, exact data on propagation speed of ultrasonic waves through liquid components have not been obtained except for representative components such as water and so on for which detailed data have been obtained including the temperature and pressure dependency. In addition, the temperature dependency of sonic speed in a liquid exhibits a large value which may be several times higher than that in a solid member. Moreover, when the liquid is a solution, sonic speed is susceptible to fluctuations also due to a change in components of the solution. For the reasons set forth above, the temperature and pressure compensation method of the present invention treats sonic speed in a fluid under measurement at temperature and pressure under a service condition as an unknown value which is to be derived, based on the measured propagation times of ultrasonic waves between the ultrasonic transducers, using the above-mentioned known data.

In the approximate calculation of the present invention for determining the refraction angle $\theta_f$ of sonic waves from the pipe wall to the fluid and the propagation time $\tau$ of ultrasonic waves through the oblique wedge of each ultrasonic transducer in the basic Equation (6) for calculating a flow velocity, Equation (14) is first employed to calculate a first approximate value $\tau_1$ of the propagation time $\tau$ of ultrasonic waves through the oblique wedge of the ultrasonic transducer and the pipe wall which are made of solid materials so that they exert relatively less influences on sonic speed in terms of temperature and pressure. Used as an initial value of the sonic speed/refraction angle ratio C in Equation (14) is the value $C_0$ which is calculated by substituting a sonic speed value $C_f$ in water at constant temperature and pressure, which may be searched, into the numerator of the rightmost fraction in Equation (7) and by substituting the design value of the incident angle $\theta_{fd}$ to the fluid into the incident angle $\theta_f$ of sound rays from the pipe 3 to the fluid 4, appearing in the demoninator of the rightmost fraction in Equation (7).

After first approximate values of C and $\tau$ are derived by the above calculations, these values, the measured propagation time $T_0$ of ultrasonic waves, and the distance D between the opposite inner diameter of the pipe, known from the standard or by a measurement, are substituted into Equation (14) to derive a first approximate value $C_{f1}$ of sonic speed $C_f$ in the fluid.

Next, by substituting the respective first approximate values calculated as described above and other various values known by a search, standard, or measurement into Equation (12), the projection length L of sound rays between ultrasonic transducers to the axis of the pipe is derived. However, since the sonic speed/refraction angle ratio C used for deriving the value L is the initial value $C_0$ which is different from the true value under the measuring conditions, the calculated projection length $L_c$ of sound rays is not completely identical to a measurement-based value L (which is considered to the practically measured L by the size of the ultrasonic transducers) of the projection length of sound rays derived by the use of various design values of the ultrasonic transducers based on the measured value of the spacing between the mounted positions of the ultrasonic transducers on the pipe. Thus, another value C, slightly different from the initial value $C_0$ of C used in the first approximate calculation is set as a second approximate value, and the calculations explained above are repeated with the set second approximate value to derive a second approximate value of the projection length of sound rays. If the second approximate value of C is appropriately set, the calculated value of the projection length is closer to the measurement-based value L.

When a difference between the approximately calculated value $L_{ci}$ and the measurement-based value L becomes smaller than a predetermined value after repeating the gradual approximate calculations, the sonic speed/refraction angle ratio set at that stage is designated as an approximate convergence value Ci, and this approximate convergence value Ci is applied to Equations (14), (13) and (7) to derive the respective values of $\tau$, $C_f$ and $\theta_f$. Then, a difference $\Delta T$ between the average value $T_0$ and a propagation time of ultrasonic waves derived by these values, the known distance D between the opposite inner wall surfaces of the pipe and the measurement is applied to the basic Equation (6) to calculate a flow velocity of the fluid flowing in the pipe at temperature and pressure under a service condition.

Further, a reform of Equation (6) using Equations (7) and (4) results in the following Equation (15) which shows that the flow velocity V of a fluid can be immediately derived from the measured value $T_0$, $\Delta T$ (i.e., $T_1$ and $T_2$), and the values $\tau$ and C calculated by the approximations.

[Equation (15)]

$$\begin{aligned} V &= (D/\sin 2\theta_f)(C_f \cos\theta_f/D)\{\Delta T/(T_0 - \tau)\} \\ &= (1/2)(C_f/\sin\theta_f)\{\Delta T/(T_0 - \tau)\} \\ &= (C/2)\{\Delta T/(T_0 - \tau)\} \end{aligned} \quad (15)$$

DETAILED DESCRIPTION OF THE PREFERRED EMBODIMENTS

Figure 1:
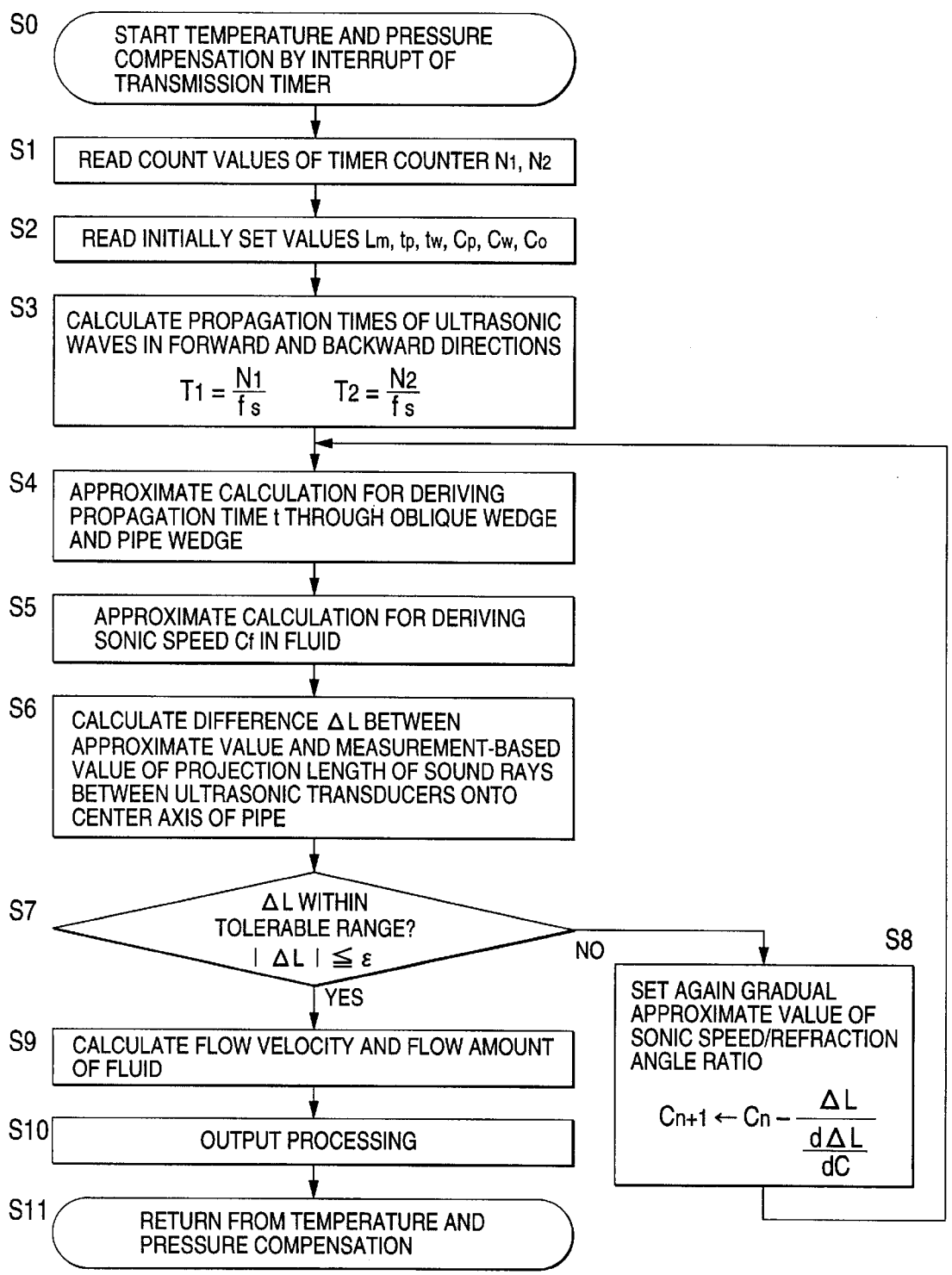
FIG. 1 is a flow diagram representing the processing for measuring and compensating a flow amount of a fluid for temperature and pressure in accordance with the present invention.
Figure 2:
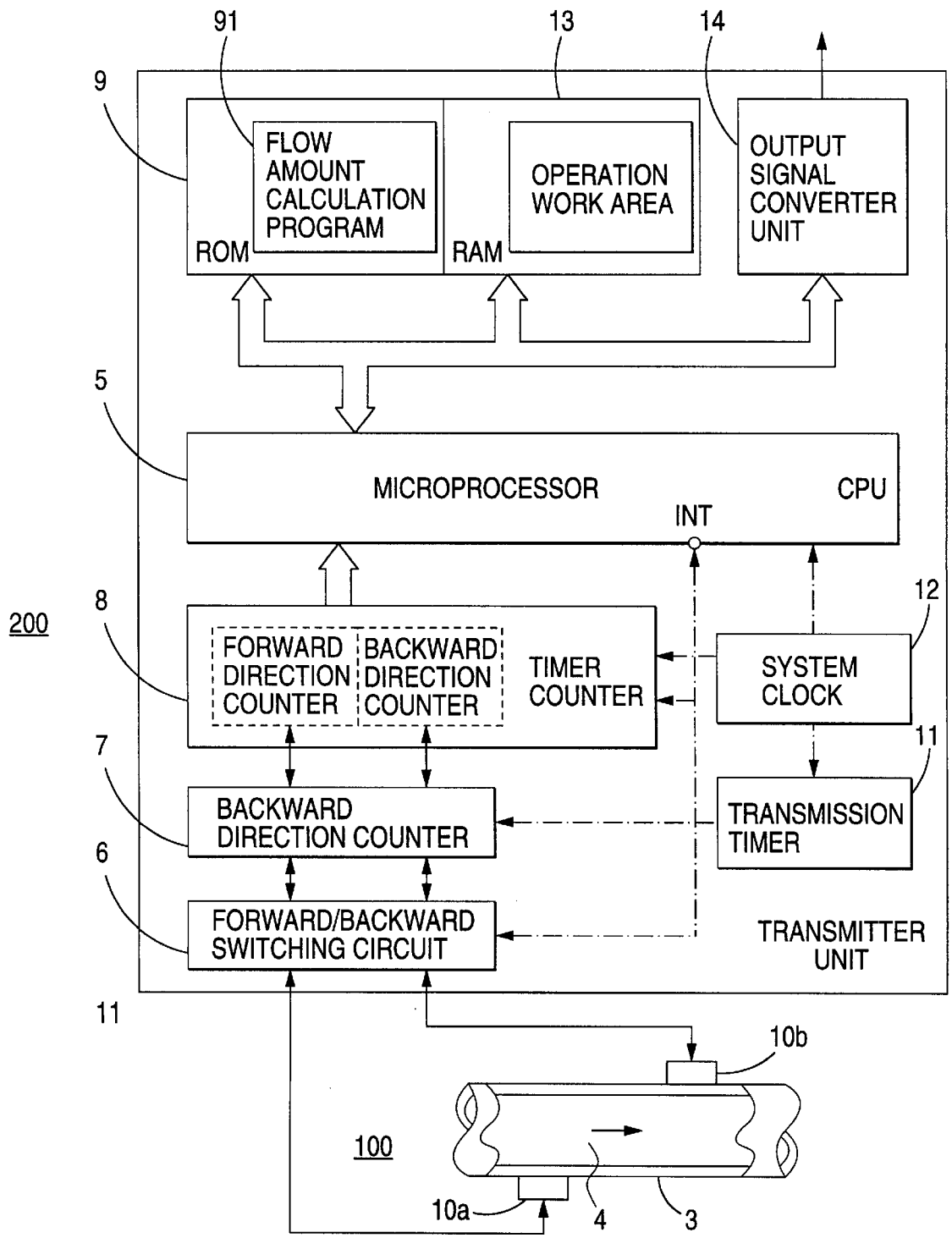
FIG. 2 is a block diagram illustrating the configuration of the transmitter unit of an ultrasonic flow meter for executing the processing of FIG. 1.

FIG. 1 represents an embodiment of a processing flow for executing a temperature and pressure compensation sequence in a clamp-on type ultrasonic flow meter according to the method of the present invention. FIG. 2 illustrates in a block diagram form an embodiment of the configuration of a transmitter unit in the ultrasonic flow meter for executing the processing flow of FIG. 1.

First, the configuration of the transmitter unit is described.

Referring specifically to FIG. 2, a transmitter unit 200 of the ultrasonic flow meter is a processing control unit for detecting an ultrasonic signal transmitted and received between ultrasonic transducers 10a, 10b mounted at their respective measuring positions on the outer wall surface of a pipe 3 to calculate a flow amount of a fluid flowing in the pipe 3. The transmitter unit 200 includes a transmitter/ receiver circuit 7 for transmitting an exciting signal for driving one of the ultrasonic transducers 10a, 10b to transmit ultrasonic waves and for amplifying an ultrasonic signal received by the other ultrasonic transducer; a forward/backward switching circuit 6 for switching the connection of the transmitter/receiver circuit 7 with the ultrasonic transducers 10a, 10b; a microprocessor 5 which operates step-by-step at timing determined by a system clock 12; a ROM 9 for storing programs executed by the microprocessor 5; a RAM 13 serving as storage means for temporarily storing numerical values and flags indicative of associated processing states which may be generated in course of the execution of programs and must be temporarily held; a transmission timer 11 for generating a period of measurements relying on the transmission and reception of ultrasonic waves based on a clock signal generated by the system clock 12; and a timer counter 8 for measuring time an interval between the ultrasonic wave transmission from one of the ultrasonic transducers and the ultrasonic wave reception by the other.

The ultrasonic flow meter is operated with the ultrasonic transducers mounted at positions on the pipe such that a maximum reception signal is generated. In this state, the spacing between the mounted positions of the pair of ultrasonic transducers in the axial direction of the pipe is measured to obtain a projection length of sound rays of the ultrasonic waves projected onto the central axis of the pipe. Then, a measurement-based value L of the projection length of the sound rays of the propagating ultrasonic waves, and the following data including a predetermined fluid used as given data in the approximate calculations, and data determined by the design of the employed ultrasonic transducers, data on the predetermined fluid, and data related to acoustic elements of the ultrasonic transducers, i.e., a distance between opposite inner wall surfaces of the pipe: D;

a thickness of the pipe: $t_p$; and a projection length of an ultrasonic wave propagating path in an oblique wedge projected onto a plane perpendicular to the center axis of the pipe: $t_w$ are inputted to the transmitter unit 200 and written into the RAM 13 as given known data.

Further, a sonic speed/refraction angle ratio $C_0$ which is the ratio of sonic speed to a sinusoidal value at the refraction angle, which is derived by substituting:

sonic speed in the oblique wedge: $C_w$ and sonic speed in the pipe wall: $C_p$ at a reference temperature, sonic speed $C_f$ in the predetermined fluid at constant temperature and pressure, and a design value $\theta_{wd}$ of an incident angle of ultrasonic waves from the pipe to the predetermined fluid into Equation (7) is calculated by searching associated acoustic data, and likewise written into the RAM 13 as an initial set value.

After mounting the ultrasonic transducers 10a, 10b at appropriate positions and writing the various data into the RAM 13, the transmitter unit 200 is started in a measurement mode. The microprocessor 5 enters an interrupt waiting state, and waits for a transmission period signal of the transmission timer 11 as an interrupt signal.

When the transmission timer 11 transmits a measurement period signal, the microprocessor 5 calls a flow amount calculation program 91 represented by the flow chart of FIG. 1 from the ROM 9. Following the flow chart, the microprocessor 5 first transfers count values $N_1$, $N_2$ of the timer counter 8 to the RAM 13 (step S1), Then, the forward/backward switching circuit 6 switches the connection between the ultrasonic transducers 10a, 10b and the transmitter/receiver circuit 7 to reverse the propagating direction of ultrasonic waves. Specifically, one of the ultrasonic transceivers 10a, 10b is set into a transmission mode to emit ultrasonic waves, and the other one is set into a reception mode. Then, a corresponding direction counter in the timer counter 8 connected to the ultrasonic transducer in the reception mode is started to measure a time interval from emission to reception of ultrasonic waves by counting periodical pulses generated by the system clock 12. After thus preparing the respective components for measurement, the processing subsequent to step S2 for calculating a flow amount is executed.

In the processing for calculating a flow amount, first, the known data and the initial set values related to the acoustic elements, which have been written into the RAM 13 as given values at the time of the installation of the ultrasonic flow meter, are read from the RAM 13 (step S2). Subsequently, with a forward direction count value $N_1$ and a backward direction count value $N_2$ read from the timer counter 8, and a frequency $f_s$ of the system clock 12, propagation times $T_1$, $T_2$ of an ultrasonic pulse signal in the forward direction and in the backward direction are calculated by the following Equation (16) (step S3):

[Equation (16)]

$$T_1 = N_1/f_s, \quad T_2 = N_2/f_s \tag{16}$$

After calculating the propagation times $T_1$, $T_2$ of the ultrasonic pulse signal from measured values by the above Equation (16), the initially set value $C_0$ of the sonic speed/refraction angle ratio, the thickness $t_p$ of the pipe wall, the projection length $t_w$ of sound rays in the oblique wedge projected onto the plane perpendicular to the axis of the pipe, and sonic speed $C_w$, $C_p$ in the pipe wall and in the oblique wedge are substituted into Equation (14) to calculate a first approximate value $\tau_1$ of a propagation time of ultrasonic waves through the pipe and oblique wedge (step S4). Further, the initially set value $C_0$ of the sonic speed/refraction angle ratio, the first approximate value $\tau_1$ of the propagation time of ultrasonic waves through the pipe and oblique wedge, the distance D between the opposite inner wall surfaces of the pipe, and the propagation time $T_0$ when the fluid is stationary, calculated by averaging the propagation times $T_1$, $T_2$ by Equation (5), are substituted into Equation (13) to derive a first approximate value $C_{f1}$, of sonic speed in the fluid (step S5).

The first approximate value $C_{f1}$ of sonic speed in the fluid derived by the foregoing calculation, the initially set value $C_0$ of the sonic speed/refraction angle ratio, the thickness $t_p$ of the pipe wall, the projection length $t_w$ of sound rays in the oblique wedge projected onto the plane perpendicular to the axis of the pipe, the distance D between the opposite inner wall surfaces of the pipe, and the sonic speed $C_p$, $C_w$ in the pipe wall and in the oblique wedge, which are likewise initially set values, are substituted into Equation (12) to derive a first approximate value $L_{c1}$ of the propagation length of sound rays of ultrasonic waves propagating between the ultrasonic transducers projected onto the center axis of the pipe. However, since the approximate values of the sonic speed/refraction angle ratio and the sonic speed in the fluid are used in the calculation of Equation (12), the calculated value $L_{c1}$ of the propagation length of sound rays of ultrasonic waves propagating between the ultrasonic transducers projected onto the center axis of the pipe is not generally coincident with the measurement-based value L of the propagation length obtained by actually measuring the spacing between the mounted positions of the ultrasonic transducers. Thus, by again repeating the foregoing steps of the approximate calculations with the sonic speed/refraction angle ratio set at a value slightly different from the initial value $C_0$, an approximate value $L_{ci}$ closer to the measurement-based value L can be derived (steps S6–S8).

When the difference $\Delta L$ between the measurement-based value L and the approximate value $L_{ci}$ of the projection length of sound rays of ultrasonic waves projected onto the center axis of the pipe is decreased below a predetermined value while repeating the steps of the foregoing approximate calculations, a value of the sonic speed/refraction angle ratio at that approximation stage is designated as an approximate convergence value Ci. Then, the approximate value $\tau_i$ of the propagation time of ultrasonic waves through the pipe and the oblique wedge calculated by Equation (14) corresponding to the approximate convergence value Ci, an approximate value $\theta_{fi}$ of the refraction angle of ultrasonic waves from the pipe to the fluid calculated through Equation (7), the distance D between the opposite inner wall surfaces of the pipe which is an initial set value, and the difference $\Delta T$ of the propagation times of ultrasonic waves between the ultrasonic transducers in the forward and backward directions obtained by a measurement, and the average value $T_0$ corresponding to the propagation time of ultrasonic waves through the fluid in a stationary state are substituted into Equation (6) to derive the flow velocity V at temperature and pressure under the measuring conditions. This flow velocity value is used to calculate and output the flow amount value (steps S9, S10), followed by exiting the processing started by an interrupt (step S11).

The approximate calculation for minimizing the difference $\Delta L$ between a calculated value $L_c$, with the sonic speed/refraction angle ratio C of the projection length of the spacing between the mounted positions of the ultrasonic transducers projected onto the center axis of the pipe as a variable, and the projection length L obtained by an actual measurement is nothing but a calculation for deriving the root of the following functional Equation (17) for a variable C derived from Equation (12) by approximation:
[Equation (17)]

$$\Delta L_c = L_c - L = 0 \qquad (17)$$

$$\therefore$$

$$2t_w \left( C_w / \sqrt{C^2 - C_w^2} \right) + 2t_p \left( C_p / \sqrt{C^2 - C_p^2} \right) +$$

$$D \left( C_f / \sqrt{C^2 - C_f^2} \right) - L = 0$$

An application of Newton's sequential approximation method to the approximate calculation for deriving the root of the above functional equation enables an efficient accomplishment of the approximate calculation. For this purpose, Equation (17) is differentiated for the variable C to derive a differential function $\Delta L'_c$ of the function $\Delta L_c$. The differential function $\Delta L'_c$ and the original function $\Delta L_c$ are applied to Equation (18) which is the formula of Newton's sequential approximation. $C_0$ calculated as an initially set value of the sonic speed/refraction angle ratio is designated as an initial value of the root, Equation (18) is repetitively applied to derive a high-order approximate solution.
[Equation (18)]

$$C_{n+1} = C_n - \Delta L_c / [d_\Delta L_c / dC]_{C=C_n} (n=0, 1, 2,) \qquad (18)$$

Incidentally, the last portion in Equation (15) indicates that an average flow velocity of a fluid on sound rays is expressed without using the refraction angle $\theta_f$ of ultrasonic waves from the pipe to the fluid derived through Equation (7). Thus, using the approximate convergence value Ci of the sonic speed/refraction angle ratio derived by the gradual approximate calculation and the approximate value $\tau_i$ of the propagation time of ultrasonic waves through the pipe wall and the oblique wedge derived in correspondence to this value Ci, the flow amount of the fluid in the pipe can be obtained without the calculation for deriving the incident angle $\theta_f$ of ultrasonic waves from the pipe to the fluid based on Equation (15).

Also, if the diameter of the pipe is so large that the propagation time $\tau$ of ultrasonic waves through the oblique wedge and the pipe wall is sufficiently small as compared with the average time $T_0$ of the propagation times of ultrasonic waves between the ultrasonic transducers, the propagation time $\tau$ of ultrasonic waves through the oblique wedge and the pipe wall will not influence so much on a measurement accuracy, so that even if the most probable value of the sonic speed/refraction angle ratio only is derived by the gradual approximate calculation and the propagation time $\tau$ is treated as a given constant value, without deriving the propagation time $\tau$ by an approximate calculation, the flow amount of the fluid may be calculated as a result at practically tolerable accuracy.

Further, if data on the temperature dependency of sonic speed in at least one of the oblique wedge and the pipe is known in detail, a means for storing the temperature dependency data and a means for measuring the temperature of at least one of the oblique wedge and the pipe or a physical amount equivalent to temperature may be provided, such that the known temperature dependency data stored in the storing means is searched based on a physical amount measured by the temperature detecting means, the most probable value Ci of the sonic speed/refraction angle ratio is calculated by the gradual approximate calculation using the searched value, and the flow amount of the fluid is obtained using the thus derived Ci.

The foregoing temperature and pressure compensation method for an ultrasonic flow meter according to the present invention may be summarized as follows. Sonic speed in a fluid under measurement having large and temperature dependency and an incident angle of sonic waves from a pipe to the fluid depending on the sonic speed are designated as basic unknown variables. The values of these unknown variables are derived by gradual approximate calculations using a projection length of sound rays of ultrasonic waves propagating between ultrasonic transducers projected onto the center axis of the pipe, determined by an actual measurement when the ultrasonic transducers are mounted at measuring positions on the pipe for the installation of the ultrasonic flow meter, and previously known given data on the pipe including the inner diameter thereof and so on and on acoustic members constituting the ultrasonic transducers. The sonic speed of ultrasonic waves derived by the approximate calculation and the incident angle of ultrasonic waves from the pipe to the fluid are applied to a basic equation for calculating a flow velocity of the fluid from a propagation time of ultrasonic waves obtained by an acoustic measurement to derive the flow velocity of the fluid in the pipe on which the ultrasonic flow meter is installed. Thus, even if data indicating the influence of temperature and pressure on sonic speed in the fluid under measurement are not previously provided, no measurements of temperature and pressure of the fluid under measurement are required. Instead, the propagation time obtained by an acoustic measurement and various values determined by the design of the ultrasonic transducers and the pipe on which the ultrasonic flow meter is installed may be used to correct the sonic speed in terms of the influences of temperature and pressure, thus achieving a true value of the flow velocity of the fluid under measurement.

In addition, when Newton's sequential approximation method is applied to the approximate calculation for deriving an approximate convergence value of the sonic speed/refraction angle ratio which is an unknown variable, the most probable value of the sonic speed/refraction angle ratio can be reached with less calculation steps as compared with an approximate calculation executed with randomly set sonic speed/refraction angle ratio. Further, when the flow amount of a fluid in the pipe is derived based on the sonic speed/refraction angle ratio calculated by a gradual approximate calculation without using a calculation for deriving an incident angle of ultrasonic waves from the pipe to the fluid, the processing speed is increased due to the elimination of the calculation for deriving the incident angle.

Similarly, when the diameter of a pipe on which the ultrasonic transducers are mounted is so large that a propagation time of ultrasonic waves through the oblique wedge and the pipe wall is sufficiently small as compared with an average time of the propagation times of ultrasonic waves between the ultrasonic transducers, an approximate convergence value of the sonic speed/refraction angle ratio may be derived by a gradual approximate calculation, with the propagation time treated as a given constant value, to obtain the flow amount of the fluid. In this calculation process, a compensated result can be derived with a less number of steps since approximate calculation steps for calculating the propagation time of ultrasonic waves through the oblique wedge and the pipe are omitted.

Furthermore, if data on temperature dependency of sonic speed in the oblique wedge or the pipe is known in detail, a means for storing the temperature dependency data and a means for measuring the temperature of the oblique wedge or the pipe may be provided, such that the known temperature dependency data stored in the storing means is searched on a detected temperature value, the most probable value Ci of the sonic speed/refraction angle ratio is calculated by a gradual approximate calculation using the searched value, and the flow amount of the fluid is obtained using the thus derived Ci, thereby rendering it possible to obtain a flow amount compensated for the temperature dependency of sonic speed in the oblique wedge and the pipe, and hence a measurement result at higher accuracy.

In continuation, specific effects produced by the present invention will be described with reference to graphs illustrated in FIGS. 3–5.

Figure 3A:
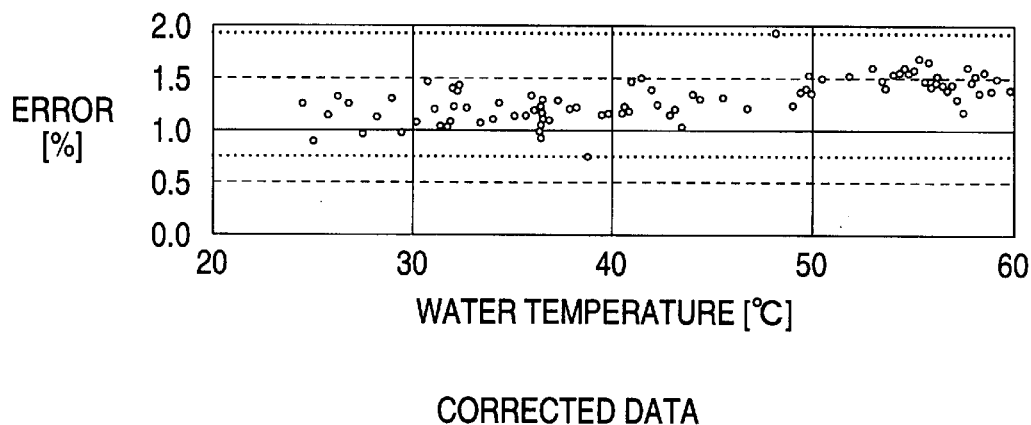
FIGS. 3A and 3B are graphs illustrating an example of effects of a compensation performed for changes in temperature of water.
Figure 3B:
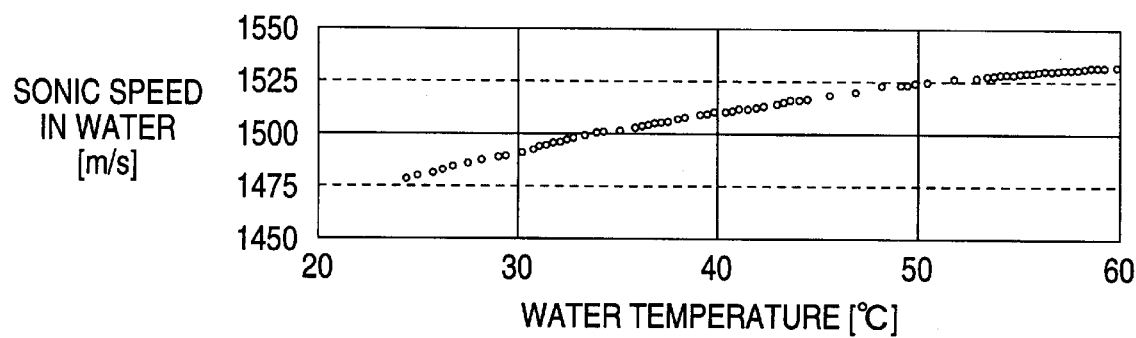

FIGS. 3A, and 3B represent the results of measuring flow amounts of waters at different temperatures, to which the compensation method of the present invention is applied, wherein a pair of ultrasonic transducers are mounted with a spacing of 117.2 mm therebetween on the outer wall surface of a circular pipe made of stainless steel having an inner diameter of 101.7 mm and a thickness of 5.0 mm, through which the water is flowing.

Figure 7:
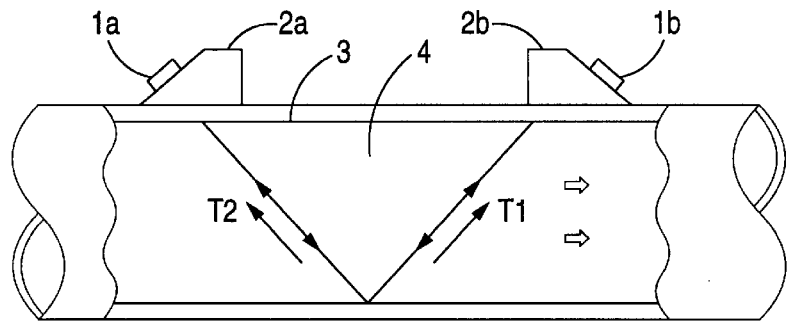
FIG. 7 is a diagram illustrating the configuration of a detector unit of a V-shaped clamp-on type ultrasonic flow meter.
Figure 8:
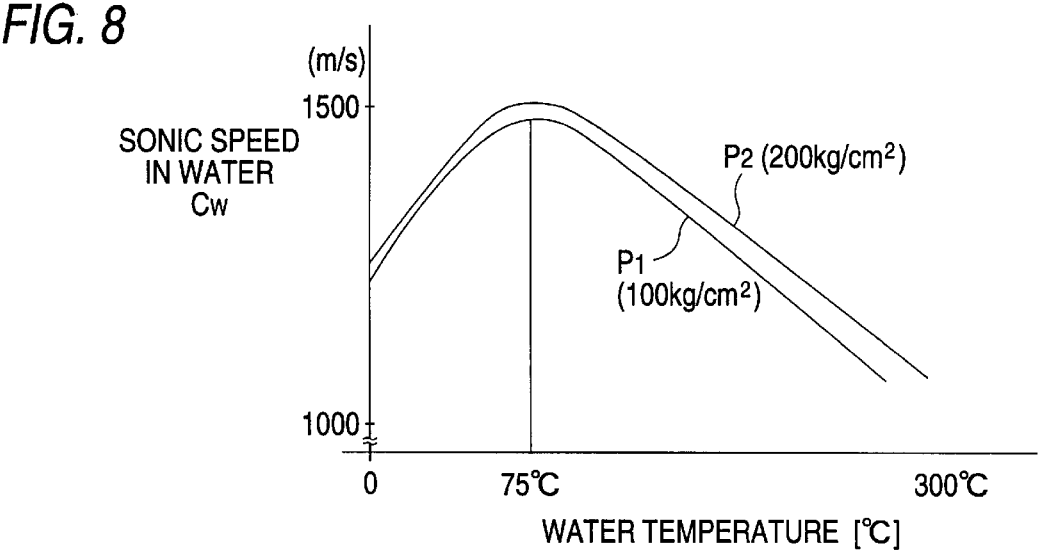
FIG. 8 is a graph representing the influence of temperature and pressure exerted on the sonic water through water (a graph quoted from Steam Tables 1980 published by Japan Society of Mechanical Engineers).
Figure 9:
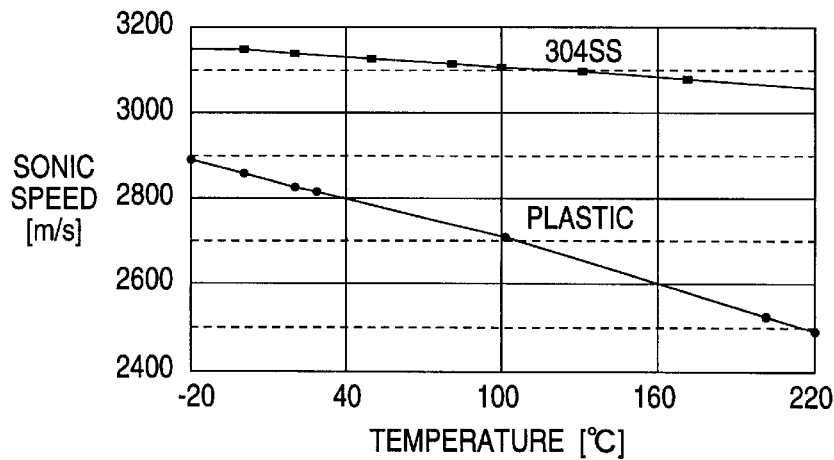
FIG. 9 is a graph representing an example of the relationship between sonic speed in a solid material and temperature.

In this example, the ultrasonic transducers are mounted in the V-shape configuration as illustrated in FIG. 7, and the circuit configuration as illustrated in FIG. 2 is employed for a circuit for measuring a propagation time. The flow velocity of water through the pipe is set at 85 m³/h (corresponding to an average flow velocity of approximately 3 m/s on the pipe cross-section). The pressure of water is set at approximately 0.2 MPa, and the temperature of water is varied from 24° C. to 60° C.

FIG. 3A illustrates corrected data of the ultrasonic flow meter on a coordinate system having the abscissa representing water temperature and the ordinate representing errors produced by the flow meter. FIG. 3B plots measurement results on a coordinate system having the abscissa likewise representing water temperature and the ordinate representing sonic speed in water obtained by the present invention. It can be understood from these results that while the sonic speed in water increases as the water temperature rises, errors introduced in the measurements of the flow amount are hardly influenced by the rise of the water temperature.

Figure 4A:
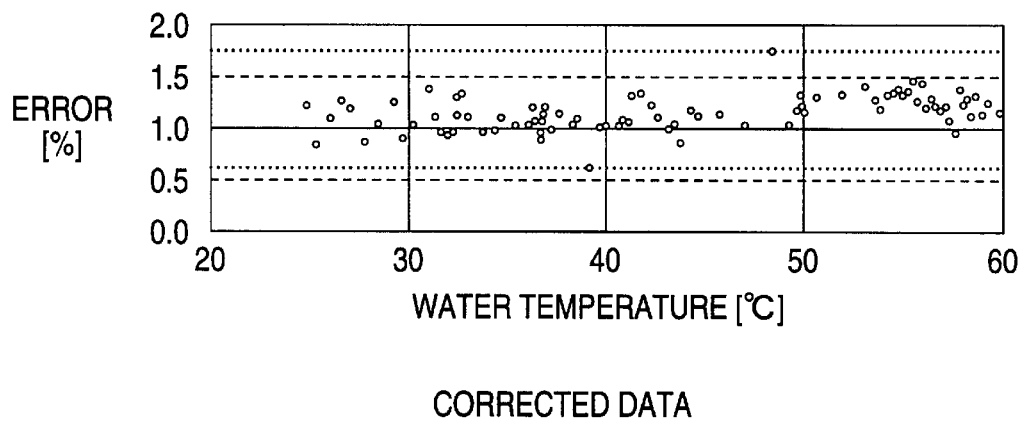
FIGS. 4A and 4B are graphs illustrating another example of effects produced by the compensation.
Figure 4B:
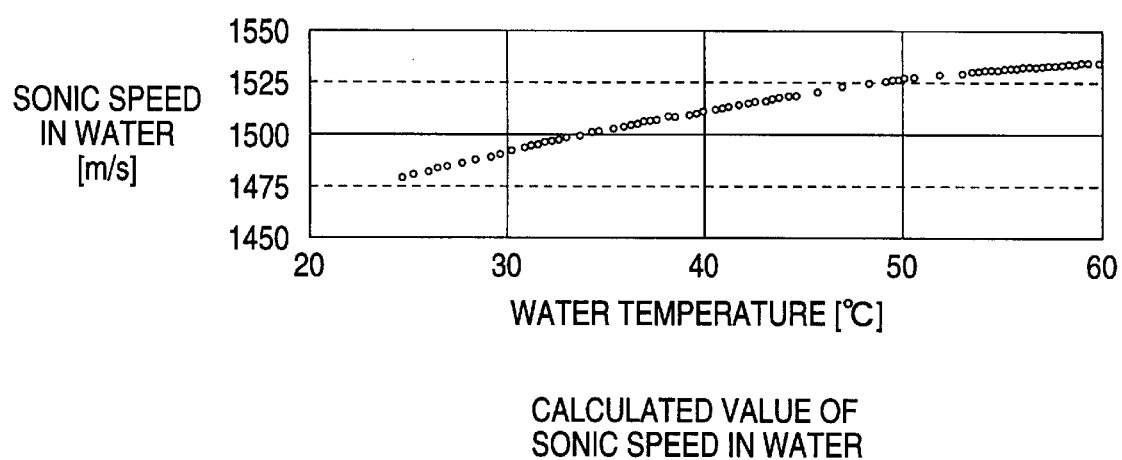

Turning next to FIGS. 4A and 4B, illustrated therein are the results of a temperature correction performed on sonic speed in the oblique wedge and the pipe using data on temperature dependency of sonic speed in the oblique wedge, in addition to the data on propagation time measured by the circuit configuration illustrated in FIG. 2. Assuming that fluid temperature is x [°C.] and the error is y [%], a recursive line is expressed by Equation (19) for FIG. 3A illustrating the results of flow amount measurements without performing a temperature correction on sonic speed using the results of detecting temperatures of the oblique wedge and the pipe:
[Equation (19)]

$$y=0.0128x+0.7571 \qquad (19)$$

Whereas a recursive line as expressed by Equation (20) is given for FIG. 4A which illustrates the results of flow amount measurements in which sonic speed in the oblique wedge and the pipe is corrected in terms of temperature:
[Equation (20)]

$$y=0.0070x+0.8534 \qquad (20)$$

It can be understood from the above equations that the dependency of sonic speed on temperature of the fluid is further reduced by performing the temperature correction on sonic speed in the oblique wedge and the pipe material.

Figure 5:
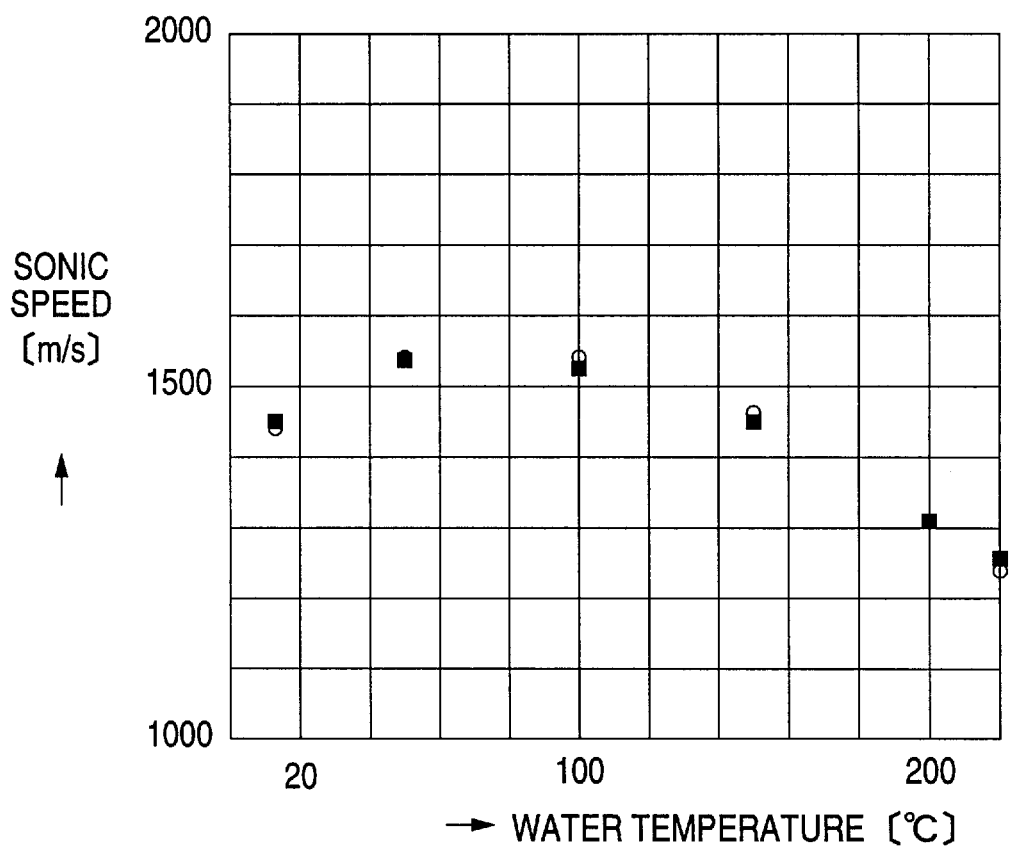
FIG. 5 is a graph illustrating an example of effects of a compensation performed for changes in temperature and pressure of a fluid.
Figure 6A:
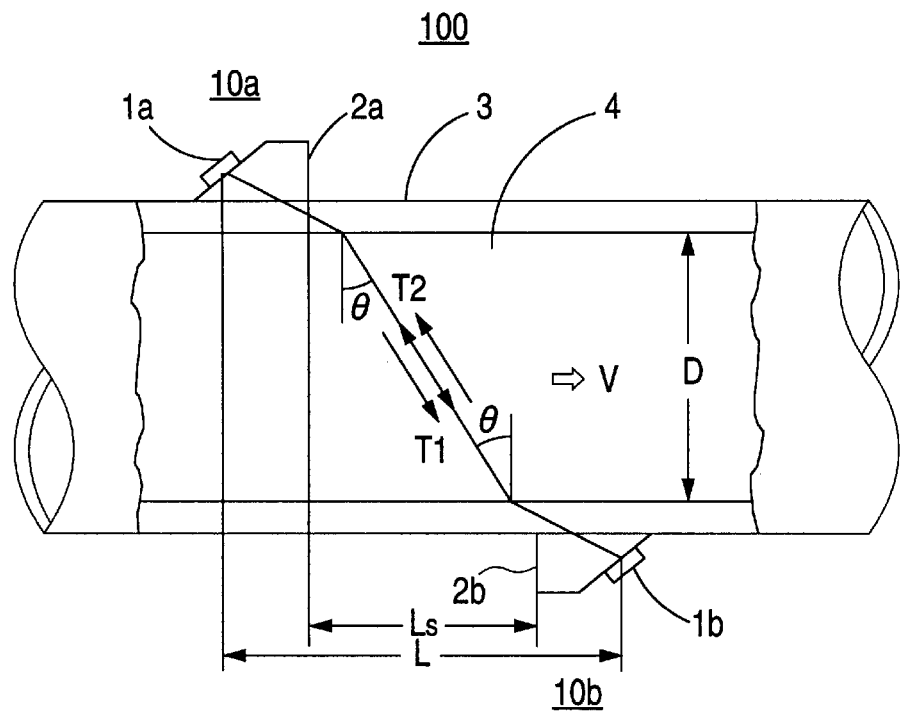
FIGS. 6A and 6B are diagrams illustrating the configuration of a detector unit of a clamp-on type ultrasonic flow meter.
Figure 6B:
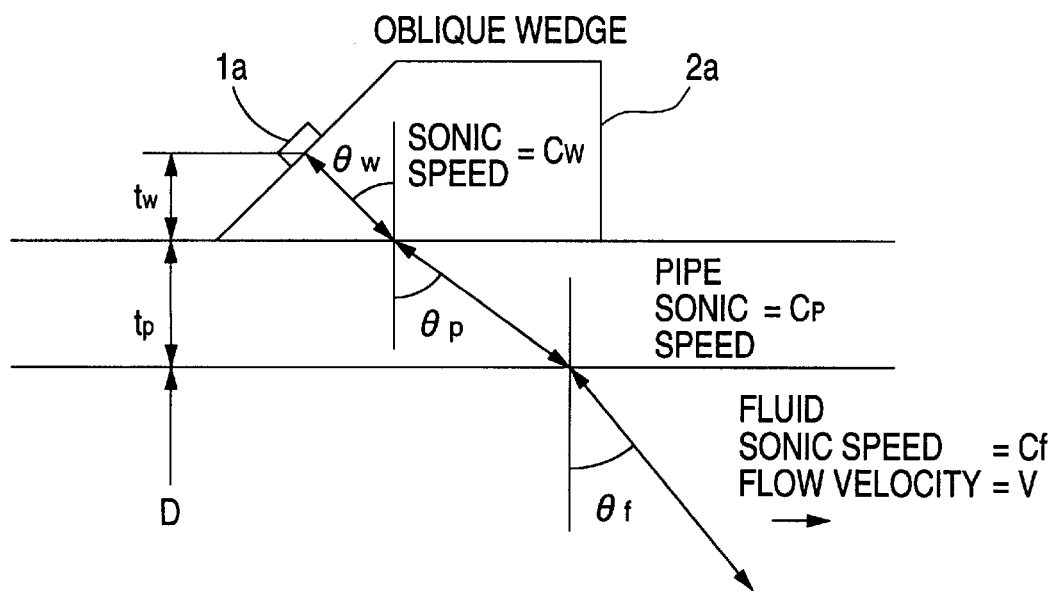

Referring next to FIG. 5, there is illustrated the results of correcting sonic speed in water, according to the method of the present invention, where a pair of ultrasonic transducers are mounted with a spacing of 71.4 mm therebetween on the outer wall surface of a circular pipe made of stainless steel having an inner diameter of 54.9 mm and a thickness of 6.1 mm. In this state, the pressure of water in the pipe, not flowing, is varied in a stepwise manner (pressurized to the atmospheric pressure or more at temperature equal to or higher than 100° C.) to change the water temperature from 16° C. to 220° C., and sonic speed in water is measured, using the compensation method of the present invention, with various values which have been known at the time of the mounting of the ultrasonic transducers and a measured propagation time of ultrasonic waves through stationary water. It should be noted that in this example, the ultrasonic transducers are likewise mounted in the V-shape configuration as illustrated in FIG. 7.

FIG. 5 illustrates the calculation results of sonic speed in water derived by processing measured values of the propagation times of ultrasonic waves in accordance with the method of the present invention together with theoretically calculated data obtained by referring to the aforementioned steam tables for the purpose of comparison. The comparison data are obtained by interpolation based on data listed in the steam tables on sonic speed in water at the same pressure and temperature as the experiment.

As can be seen from FIG. 5, the difference between the sonic speed values measured and applied with the compensation method of the present invention and the literature-based comparison data is merely within ±1.4%, thus clarifying that the compensation method according to the present invention is effective for compensating sonic speed for changes in pressure of a fluid in addition to changes in temperature of the fluid.

What is claimed is:

1. A temperature and pressure compensation method in a clamp-on type ultrasonic flow meter comprising
    a pair or more of ultrasonic transducers each including an ultrasonic oscillator and an oblique wedge, and mounted on the outer peripheral surface of a pipe in which a fluid is flowing, and
    a measurement control unit for calculating for measuring propagation times of ultrasonic waves propagating in a flow direction and in the reverse direction of the fluid flow, and outputting a flow amount of the fluid based on the propagation times,
    said method comprising the steps:
    (A) preparing, as given known data:
        (a) a distance between opposite inner wall surfaces or outer wall surfaces on a plane of the pipe through which ultrasonic waves transmit, and a thickness of the pipe wall;
        (b) a length of a propagation path of ultrasonic waves through the oblique wedge of the ultrasonic transducer projected onto a plane perpendicular to the center axis of the pipe;
        (c) a length of a propagation path of ultrasonic waves between the ultrasonic transducers projected onto the center axis of the pipe;
        (d) sonic speed in the oblique wedges at a reference temperature; and
        (e) sonic speed in the pipe wall of the pipe at the reference temperature;
    (B) calculating an approximate convergence value of a sonic speed/refraction angle ratio, which is a ratio of sonic speed to a sinusoidal value at the refraction angle of the ultrasonic wave from the pipe to the fluid in the fluid existing in the pipe at temperature and pressure under measuring conditions, based on the measured propagation times of the ultrasonic waves in the forward direction and backward direction with respect to the fluid flow, using said given known data, by a gradual approximate calculation; and
    (C) applying an incident angle of the ultrasonic waves to the fluid existing in the pipe derived by said gradual approximate calculation and the propagation time of the ultrasonic waves passing through the oblique wedge and the pipe wall to a calculation equation for deriving a flow velocity of the fluid existing in the pipe from the measured propagation times of the ultrasonic waves in the fluid flowing direction and in the reverse direction to calculate a flow amount of the fluid existing in the pipe at temperature and pressure under the measuring conditions.

2. The temperature and pressure compensation method of claim 1, further comprising a step of:
    (D) calculating an incident angle of the ultrasonic waves from the pipe to the fluid derived by the approximate convergence value of said ultrasonic refraction ratio or a trigonometric function thereof, and a propagation time of the ultrasonic waves passing through the oblique wedge of the ultrasonic transducer and the pipe wall.

3. The temperature and pressure compensation method of claim 1, wherein:
    the propagation time of the ultrasonic waves through the oblique wedge and the pipe is treated as a given constant value in the gradual approximate calculation.

4. The temperature and pressure compensation method of claim 2, wherein:
    the propagation time of the ultrasonic waves through the oblique wedge and the pipe is treated as a given constant value in the gradual approximate calculation.

5. The temperature and pressure compensation method of claim 1, wherein:
    an equation $$C_{n+1}=C_n-\Delta L_c/[d\Delta L_c/dC]_{C=C_n} (n=0, 1, 2,)$$

C : sonic speed/refraction angle ratio
    $L_c$: calculated value of propagation length of the ultrasonic wave projected onto the center axis of the pipe is satisfied in the gradual approximate calculation.

6. The temperature and pressure compensation method of claim 1, comprising the steps of:
    measuring temperature of at least one of the oblique wedge and the pipe or a physical amount equivalent to temperature;
    storing known data on temperature dependency of sonic speed in at least one of the oblique wedge and the pipe; and
    compensating for the temperature dependency of at least one of propagation times of ultrasonic waves through the oblique wedge and through the pipe by the use of the physical amount measured by said step of measuring temperature or a physical amount equivalent to temperature, and the known data on temperature dependency of sonic speed stored in said step of storing.

7. A clamp-on type ultrasonic flow meter comprising:
    a pair or more of ultrasonic transducers each including an ultrasonic oscillator and an oblique wedge, and mounted on the outer peripheral surface of a pipe in which a fluid is flowing, and
    a measurement control unit for calculating for measuring propagation times of ultrasonic waves propagating in a flow direction and in the reverse direction of the fluid flow, and outputting a flow amount of the fluid based on the propagation times, comprising:
    (A) means for preparing, as given known data:
        (a) a distance between opposite inner wall surfaces or outer wall surfaces on a plane of the pipe through which ultrasonic waves transmit, and a thickness of the pipe wall;
        (b) a length of a propagation path of ultrasonic waves through the oblique wedge of the ultrasonic transducer projected onto a plane perpendicular to the center axis of the pipe;
        (c) a length of a propagation path of ultrasonic waves between the ultrasonic transducers projected onto the center axis of the pipe;
        (d) sonic speed in the oblique wedges at a reference temperature; and
        (e) sonic speed in the pipe wall of the pipe at the reference temperature;
    (B) means for calculating an approximate convergence value of a sonic speed/refraction angle ratio, which is a ratio of sonic speed to a sinusoidal value at the refraction angle of the ultrasonic wave from the pipe to the fluid in the fluid existing in the pipe at temperature and pressure under measuring conditions, based on the measured propagation times of the ultrasonic waves in the forward direction and backward direction with respect to the fluid flow, using said given known data, by a gradual approximate calculation; and (C) means for applying said incident angle of the ultrasonic waves to the fluid existing in the pipe derived by said gradual approximate calculation and the propagation time of the ultrasonic waves passing through the oblique wedge and the pipe wall to a calculation equation for deriving a flow velocity of the fluid existing in the pipe from the measured propagation times of the ultrasonic waves in the fluid flowing direction and in the reverse direction to calculate a flow amount of the fluid existing in the pipe at temperature and pressure under the measuring conditions.

8. The clamp-on type ultrasonic flow meter of claim 7, further comprising:

(D) means for calculating an incident angle of the ultrasonic waves from the pipe to the fluid derived by the approximate convergence value of said ultrasonic refraction ratio or a trigonometric function thereof, and a propagation time of the ultrasonic waves passing through the oblique wedge of the ultrasonic transducer and the pipe wall.

9. The clamp-on type ultrasonic flow meter of claim 7, wherein:

the propagation time of the ultrasonic waves through the oblique wedge and the pipe is treated as a given constant value in the gradual approximate calculation.

10. The clamp-on type ultrasonic flow meter of claim 8, wherein:

the propagation time of the ultrasonic waves through the oblique wedge and the pipe is treated as a given constant value in the gradual approximate calculation.

11. The clamp-on type ultrasonic flow meter of claim 7, wherein:

an equation $$C_{n+1}=C_n-\Delta L_c/[d\Delta L_c/dC]_{C-Cn}(n0, 1, 2,)$$

C : sonic speed/refraction angle ratio $L_c$: calculated value of propagation length of the ultrasonic wave projected onto the center axis of the pipe is satisfied in the gradual approximate calculation.

12. The clamp-on type ultrasonic flow meter of claim 7, comprising:

means for measuring temperature of at least one of the oblique wedge and the pipe or a physical amount equivalent to temperature;

means for storing known data on temperature dependency of sonic speed in at least one of the oblique wedge and the pipe; and means for compensating for the temperature dependency of at least one of propagation times of ultrasonic waves through the oblique wedge and through the pipe by the use of the physical amount measured by said means for measuring temperature or a physical amount equivalent to temperature and the known data on temperature dependency of sonic speed stored in said storing means.

13. The clamp-on type ultrasonic flow meter of claim 7, wherein:

the pair or more of ultrasonic transducers are mounted on the same side of the pipe.

14. The clamp-on type ultrasonic flow meter of claim 7, wherein:

the pair or more of ultrasonic transducers are mounted on the opposite side of the pipe.

\* \* \* \* \*